(12) United States Patent
Chen

(10) Patent No.: US 8,067,468 B2
(45) Date of Patent: Nov. 29, 2011

(54) L-CARNITINE AND ALKANOYL L-CARNITINE PHYTATES AND PROCESS FOR PREPARING THE SAME

(76) Inventor: Jian Chen, Diamond Bar, CA (US)

( * ) Notice: Subject to any disclaimer, the term of this patent is extended or adjusted under 35 U.S.C. 154(b) by 251 days.

(21) Appl. No.: 12/584,769

(22) Filed: Sep. 12, 2009

(65) Prior Publication Data

US 2010/0317890 A1    Dec. 16, 2010

(51) Int. Cl.
*A61K 31/225*    (2006.01)
*A61K 31/205*    (2006.01)
*C07C 69/66*    (2006.01)
*C07C 229/24*    (2006.01)

(52) U.S. Cl. ......... 514/547; 514/556; 560/176; 562/575

(58) Field of Classification Search ................... 514/547, 514/556; 560/176; 562/575
See application file for complete search history.

(56) References Cited

U.S. PATENT DOCUMENTS 6,703,042 B1   3/2004   Buononato
2006/0241181 A1   10/2006   Pola

OTHER PUBLICATIONS

PCT International Search Report for International Application No. PCT/US2009/003522, all pages.
U.S. Appl. No. 61/061,956, Jian Chen.
Gregory S. Kelly, L-Carnitine: Therapeutic Applications of a Conditionally-Essential Amino Acid, Alternative Medical Review, 1998, pp. 345-360, vol. 3.
Inositol Hexaphosphate, Alternative Medical Review, 2002, pp. 244-248, vol. 7.
Anthony J.R. Costello, et al., P Nuclear Magnetic Resonance-pH Titrations Of Myo-Inositol Hexaphosphate, Carbohydrate Research, 1976, pp. 159-171, 46.
C. Vogt, et al., Enantiomeric Separation of D/L-Carnitine using HPLC and CZE after Derivatization, 1995, pp. 287-295, vol. 40.

*Primary Examiner* — Peter O Sullivan

(57) ABSTRACT

Salts of L-carnitine and alkanoyl L-carnitines with phytic acid of general formula (I), and the process of preparing the same, wherein the mole ratio between the L-carnitine or its alkanoyl derivatives cation and phytic acid anion be within the range of 1:1 to 6:1, wherein: $n=1\text{-}6$; $R_1$ is the phytate anion; R is either hydrogen, a straight alkanoyl group having 2-12 carbon atoms or a branched-chain alkanoyl group having 2-12 carbon atoms.

General Formula (I)

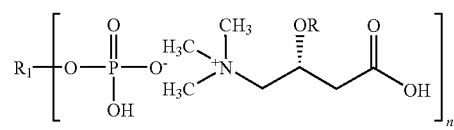

17 Claims, No Drawings

L-CARNITINE AND ALKANOYL L-CARNITINE PHYTATES AND PROCESS FOR PREPARING THE SAME

CROSS-REFERENCE TO RELATED APPLICATION

This application claims priority to PCT application US 2009/003522, filed on Jun. 10, 2009, which claims priority from U.S. Provisional Application No. 61/061,956, entitled "L-Carnitine and Alkanoyl L-Carnitine Phytates and Process for Preparing Same", filed on Jun. 16, 2008. The entire content of these applications is incorporated herein by reference.

TECHNICAL FIELD

The present invention relates to novel salt form clusters of L-carnitine and alkanoyl L-carnitine, i.e., L-carnitine phytate and alkanoyl L-carnitine phytates, and the process for preparing the same.

BACKGROUND

It is well known that L-carnitine and its alkanoyl derivatives lend themselves to various therapeutical and nutritional uses. L-Carnitine and its alkanoyl derivatives inner salts are represented by formula:

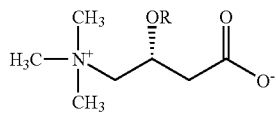

L-Carnitine or Alkanoyl L-Carnitine wherein R represents either a hydrogen atom or an alkanoyl group.

L-Carnitine is a cofactor required for transformation of free long-chain fatty acids into acylcarnitines, and for their subsequent transport into the mitochondrial matrix, where they undergo bate-oxidation for cellular energy production. Mitochondrial fatty oxidation is the primary fuel source in heart and skeletal muscles, pointing to the relative importance of the nutrient for proper function in tissue. L-Carnitine and its alkanoyl derivatives also have important antioxidant effects, as demonstrated by their protective effect against lipoperoxidation of phospholipid cell membranes caused by oxidative stress induced at the myocardial and endothelial cell level. Conditions which appear to benefit from L-carnitine and its alkanoyl derivatives include anorexia, chronic fatigue, coronary vascular disease, diphtheria, hypoglycemia, male infertility, muscular myopathies, Rett Syndrome, Alzheimer's disease, mood enhancement, cognitive improvement, and sports performance. See, e.g., Gregory S. Kelly, "L-Carnitine: Therapeutic Applications of a Conditionally-Essential Amino Acid", Alternative Medicine Review, 3 (5): 345-360 (1998).

While there are various therapeuticals and nutritional benefits of L-carnitine and its alkanoyl derivatives, much research has been carried out to improve their physical, chemical, and biological properties.

Research has primarily focused on the solutions of the physical and chemical drawbacks of L-carnitine and its alkanoyl derivatives inner salts because their hygroscopic physical characteristic creates complex problems involving the processing and storing of both the raw materials and the finished products, and their inadequate chemical stability leads to the release of traces of trimethylamine and its concomitant unpleasant fishy smell.

In these previous research, various salt forms of L-carnitine and its alkanoyl derivatives having "pharmacologically acceptable" acids as anion but without unwanted toxic or side effects have been produced, with the knowledge that the salts of L-carnitine and its alkanoyl derivates known to-date present the same therapeutical and nutritional benefits as do the so-called inner salts. Selecting suitable acid is the major endeavor in screening salt forms of L-carnitine and its alkanoyl derivatives having improved properties compared to inner salts. While various mineral acids have been tested, including hydrochloric acid, sulfuric acid, phosphoric acid, a larger number of organic acids have been tested including fumaric acid, tartaric acid, lactic acid, citric acid, malic acid, oxalic acid, orotic acid and mucic acid. While the combination of these acids with the inner salts of L-carnitine and its alkanoyl derivatives more or less satisfactorily solved the problems associated with inner salts, these salts focused on a technological solution to the purely physical or chemical drawbacks associated with L-carnitine and its alkanoyl derivatives' inner salts.

Research has been made to produce salt forms of L-carnitine and its alkanoyl derivatives with the anion moiety itself being endowed with interesting pharmacological and/or nutritional characteristics and, if possible, to synergistically enhance the therapeutical and/or nutritional properties of L-carnitine and its alkanoyl derivatives.

U.S. Patent Application Publication, No. US2006/0241181 A1 entitled "Alpha-Ketoglutarates of Active Ingredients and Compositions Containing Same" (Publication Date: Oct. 26, 2006) to Pietro Pola et al. discloses novel salt forms of L-carnitine and its alkanoyl derivatives combined with alpha-ketoglutaric acid. Alpha-ketoglutaric acid, which is a precursor to L-glutamine, plays an important metabolic role and has been successfully applied in cardiac surgery due to its important role in the Krebs cycle and, hence, in myocardial metabolism. However, according to the specification of this patent application, only honey-like pasty mass is obtained as a salt product of L-carnitine alpha-ketoglutarate and not any solid form.

Amino acids possess various therapeutical and nutritional attributes. U.S. Pat. No. 6,703,042 B1, entitled "Salts of L-Carnitine and Lower Alkanoyl L-Carnitine", (Issued: Mar. 9, 2004) to Atonietta Buononato discloses salts of L-carnitine and alkanoyl L-carnitine with amino acids, such as leucine, isoleucine, valine, cysteine, arginine and glycine to enhance therapeutical and/or nutritional efficacy with respect to their inner salts. However, as disclosed in this patent, the anion moiety (i.e., the amino acid moiety) of the salts had to be salified at the amino group with hydrochloric, or hydrobromic, and/or phosphoric acid.

In the efforts to develop new generation salt forms of L-carnitine and alkanoyl L-carnitines which not only just solve the physical and chemical drawbacks of the inner salts, but also enhance the therapeutical and/or nutritional efficacy of the inner salts, endeavors should still focus on the screening of a sophisticated acid.

Phytic acid, also known as inositol hexaphosphate, myo-inositol hexaphosphate, and IP6, is a 6-phosphate ester of inositol as represented by the molecular formula:

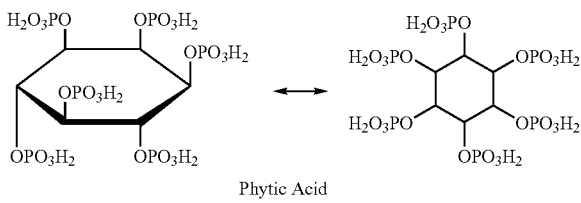

Phytic Acid

Phytic acid is naturally occurring in substantial amounts in whole grain, cereals, legumes, nuts, and seeds, and is the primary energy source for germinating plants. Phytic acid and its lower phosphorylated forms are also found in most mammalian cells, where they assist in regulating a variety of important cellular functions. Phytic acid functions as an antioxidant by chelating divalent cations such as copper and iron, preventing the generation of reactive oxygen species responsible for cell injury and carcinogenesis. Both in vivo and in vitro studies utilizing IP6 have revealed a significant anticancer activity with a variety of tumor types, possibly via inhibition of tumor cell growth and differentiation. In vitro studies with colon, liver, and rhabdomyosarcoma cell lines, and animal models of mammary, colon, intestinal, and liver cancer, as well as rhabdomyosarcoma, have all demonstrated IP6's anticancer properties. Other properties of IP6 include an anti-platelet aggregating and lipid-lowering effect, suggesting a potential health benefit for the cardiovascular system; inhibition of HIV-1 virus replication; modulation of insulin secretion in pancreatic beta cells; and inhibition of urinary calcium oxalate crystallization, thereby preventing renal stone development. See e.g. Monograph, "Inositol Hexaphosphate", Alternative Medicine Review, 7 (3): 244-248 (2002).

Other notable functions of phytic acid include the deodorant effect of body odor, bad breath or uraroma; the prevention of acute alcoholism; and the enrichment of the taste of meat and fish. These properties of phytic acid provide its pharmaceutical and/or nutritional added value.

The biochemistry and pharmacokinetics of phytic acid have also been studied. Inositol phosphates are synthesized from the parent molecule inositol and daily dietary consumption of inositol is estimated to be one gram. Once inositol reaches the cells of the intestinal tract it is phosphorylated to create inositol hexaphosphate (IP6), and then subsequently dephosphorylated to its lower forms, such as inositol pentaphosphate (IP5), inositol tetraphosphate (P4), inositol triphosphate (IP3), inositol monophosphate (IP1), which play important roles in signal transduction. Independent of the route of administration, IP6 has been discovered to be absorbed almost instantly, transported intracellularly and dephosphorylted into lower inositol phosphates. IP6 can reach targeted tumor tissue as early as one hour post-administration. When incubated with a human mammary cancer cell line, low levels of IP6 were detected as early as one minute post-incubation.

Based on its dietary derivation (i.e., it is non-toxic), its chemical properties (e.g., six phosphates attached in one inositol molecule), and its various biological activities, phytic acid is a novel acid to react with L-carnitine and alkanoyl L-carnitine inner salts to produce L-carnitine phytate and alkanoyl L-carnitine phytates. It is apparently an innovation in the evolution of salt forms of L-carnitine and salt forms of alkanoyl L-carnitine.

OBJECTS OF THE INVENTION

An object of the present invention is to provide a novel generation of L-carnitine and alkanoyl L-carnitine salt form derivatives derived from their corresponding inner salts and phytic acid, i.e., L-carnitine phytate and alkanoyl L-carnitine phytates. These salts are represented by General Formula (I):

General Formula (I)

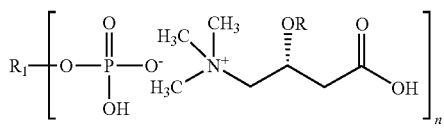

wherein $n=1-6$; $R_1$ is the phytate anion; R is hydrogen, or straight or branched-chain alkanoyl group having 2-12 carbon atoms; preferably, the alkanoyl group is a lower alkanoyl group having 2-5 carbon atoms; and more preferably, the alkanoyl group is selected from acetyl, propionyl, butyryl, isobutyryl, valeryl and isovaleryl groups.

Another object of the invention is to supply a process for the preparations of the salts represented by the formula shown in General Formula (I).

A further object of the invention is to provide the use of L-carnitine phytate and alkanoyl L-carnitine phytates.

DETAILED DESCRIPTION OF THE INVENTION

The following detailed description is directed to certain specific embodiments of the invention. However, the invention can be embodied in a multitude of different ways as defined and covered by the claims.

L-Carnitine Phytate and Alkanoyl L-Carnitine Phytates

As illustrated by the formula of phytic acid, phytic acid is a 6-phosphate ester of inositol with each phosphate group possessing 2 proton dissociation sites. There are total of 12 proton dissociation sites in one phytic acid molecule; six of which are strongly acidic with an approximate pKa value of 1.5; three sites are weakly acidic with pKa values 5.7, 6.8 and 7.6; and the remaining three sites are very weakly acidic, with pKa values greater than 10. See Costello, A. J. R., et al., "$^{31}$P-Nuclear Magnetic Resonance-pH Titrations of myo-Inositol Hexaphosphate", Carbohydrate Research, 46: 159-171 (1976). The six strongly acidic protons (with a pKa value of 1.5) are the first dissociation protons of each of the six phosphate groups in the phytic acid molecule. This dissociation ability is similar to the proton dissociations of phosphoric acid, i.e., $pKa_1$ (2.12)<$pKa_2$ (7.21)<$pKa_3$ (12.67). Dissociation of the protons of phytic acid leaves the molecule with several negative charges, which can attract positively charged molecules to generate phytate.

When phytic acid reacts with the inner salts of L-carnitine or its alkanoyl derivatives, each negatively charged phosphate group will preferably incorporate one inner salt at its quaternary ammonium cation and the corresponding phosphate dissociated proton incorporates the carboxyl anion of the inner salt. While there are 12 dissociation sites in one phytic acid molecule, theoretically, only up to 6 molecules of L-carnitine inner salt or its alkanoyl derivative inner salt can be incorporated. Because as described above, there are 6 phosphate groups in one phytic acid molecule, only the first dissociation site of each phosphate group is acidic enough (pKa 1.5) to incorporate with a inner salt to generate a corresponding salt. The other dissociation sites are too weakly acidic (with pKa values of 5.7, 6.8, 7.6, and in some instances greater than 10) to form stable ionic bonds with the quaternary ammonium cation of L-carnitine or its alkanoyl derivatives' inner salt, because the pKa value of L-carnitine's inner salt is 3.8. See, Cogt C., et al, "Enantiomeric Separation of D/L-Carnitine Using HPLC and CZE after Derivatization", Chromatographia, Vol. 40 (5/6): 287-295, (1995). So, each phosphate group of phytic acid can only incorporate 1 inner salt, and a total of 6 phosphate groups of phytic acid can incorporate a total of 6 inner salts of L-carnitine or its alkanoyl derivatives.

One phytic acid molecule can preferably incorporate 1 to 6 molecules of L-carnitine or its alkanoyl derivatives' inner salts depending on the mole ratio of added inner salts. Theoretically, when equal molar ratio of inner salt and phytic acid are added together, then the salt product will be L-carnitine phytate (in a 1:1 ratio), or alkanoyl L-carnitine phytate (in a 1:1 ratio); and similarly, when 2, 3, 4, 5 times the number of moles of inner salt are added, individually, the phytate product will be 2:1, 3:1, 4:1, and 5:1 respectively. But practically, since there are 6 same strong acidic dissociation sites in one phytic acid molecule, when an equal mole number of inner salt and phytic acid moles are added together, the phytate product is a mixture of 1:1 to 6:1 mole ratio more or less randomly created, and there is unreacted phytic acid leftover. Therefore, practically only when a 6:1 mole ratio of L-carnitine or its alkanoyl derivative inner salt and phytic acid are added together will 6 phosphate groups of phytic acid molecules fully react to obtain L-carnitine or alkanoyl L-carnitine phytate (in a 6:1 ratio). Thus, in practice a 6:1 ratio of phytate can be produced.

According to one embodiment, the mole ratios between L-carnitine cation moiety or its alkanoyl derivatives cation moiety and the phytic acid anion moiety of L-carnitine phytate or alkanoyl L-carnitine phytate can be 1:1, 2:1, 3:1, 4:1, 5:1, and 6:1, corresponding salts as represented by General Formula (I). According to one embodiment, the mole ratio is 6:1 with the salts being L-carnitine phytate (6:1) and alkanoyl L-carnitine phytates (6:1) as represented by General Formula (II):

wherein R is either hydrogen, or a straight or branched-chain alkanoyl group having 2-12 carbon atoms. According to one embodiment, the alkanoyl group is a lower alkanoyl group having 2-5 carbon atoms. According to one embodiment, the alkanoyl group is selected from acetyl, propionyl, butyryl, isobutyryl, valeryl and isovaleryl groups.

L-carnitine and alkanoyl L-carnitine phytates (in a 6:1 mole ratio) possess many desirable characteristics:

1. They are new, pure, and structurally well defined chemical compounds.

2. They contain 6 L-carnitine or alkanoyl L-carnitine molecules clustered around one phytic acid anion in one salt form of phytate (in a 6:1 mole ratio) molecule. In comparison with all the other L-carnitine or alkanoyl L-carnitine salt forms, a 6:1 mole ratio is the biggest mole ratio achieved, so far.

3. Since phytic acid is 6-phosphate ester of inositol, the stereo configuration of the salt form (6:1) is dendritic in six-directions, as a novel ionic bonded dendrimer molecule, with expected synergistic efficacy.

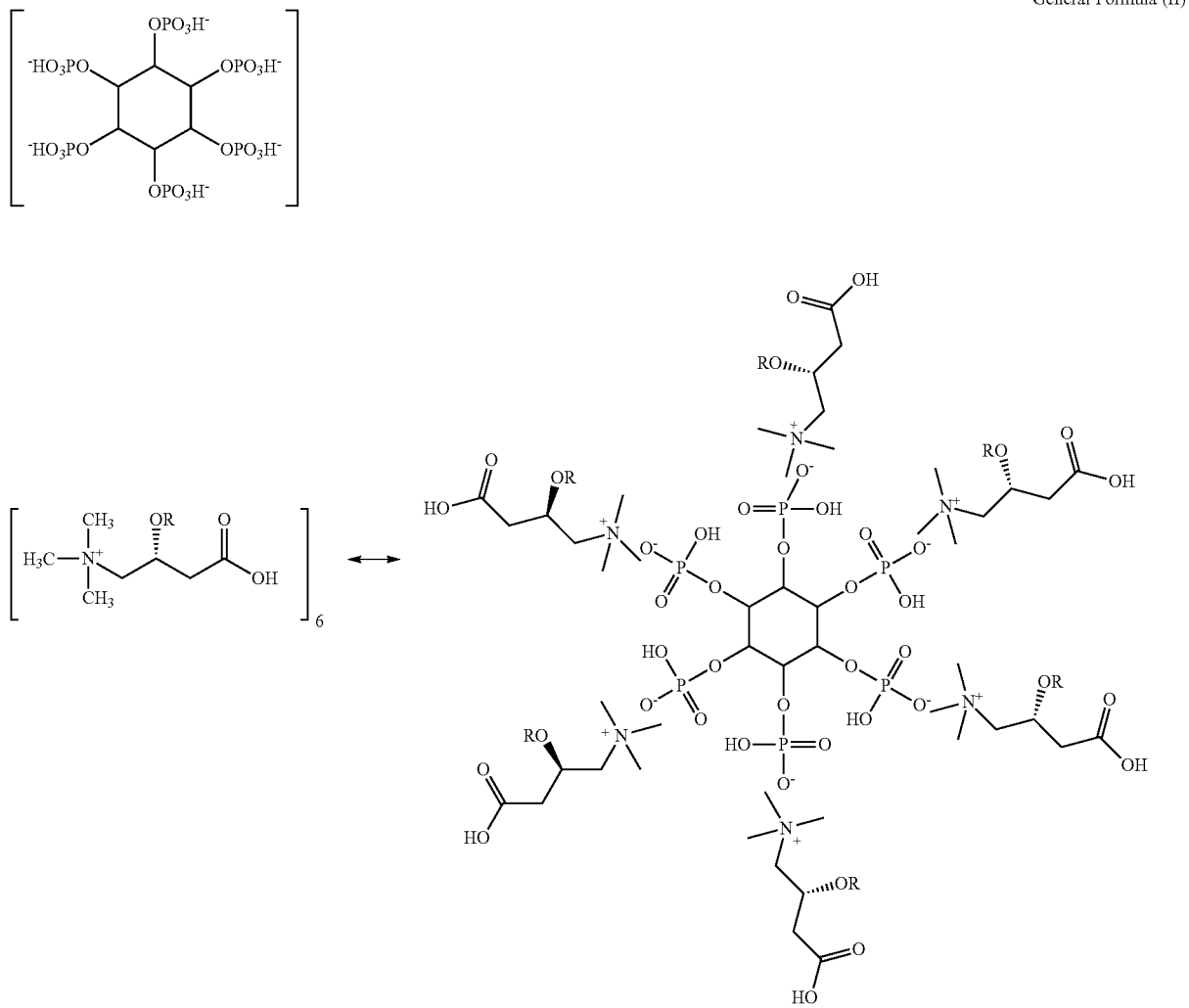

General Formula (II)

3.1. According to one embodiment, L-carnitine phytate (in a 6:1 mole ratio) ($C_{48}H_{108}N_6O_{42}P_6$, molecular weight 1627.24) is a six-directional dendrimer as shown by Formula (1):
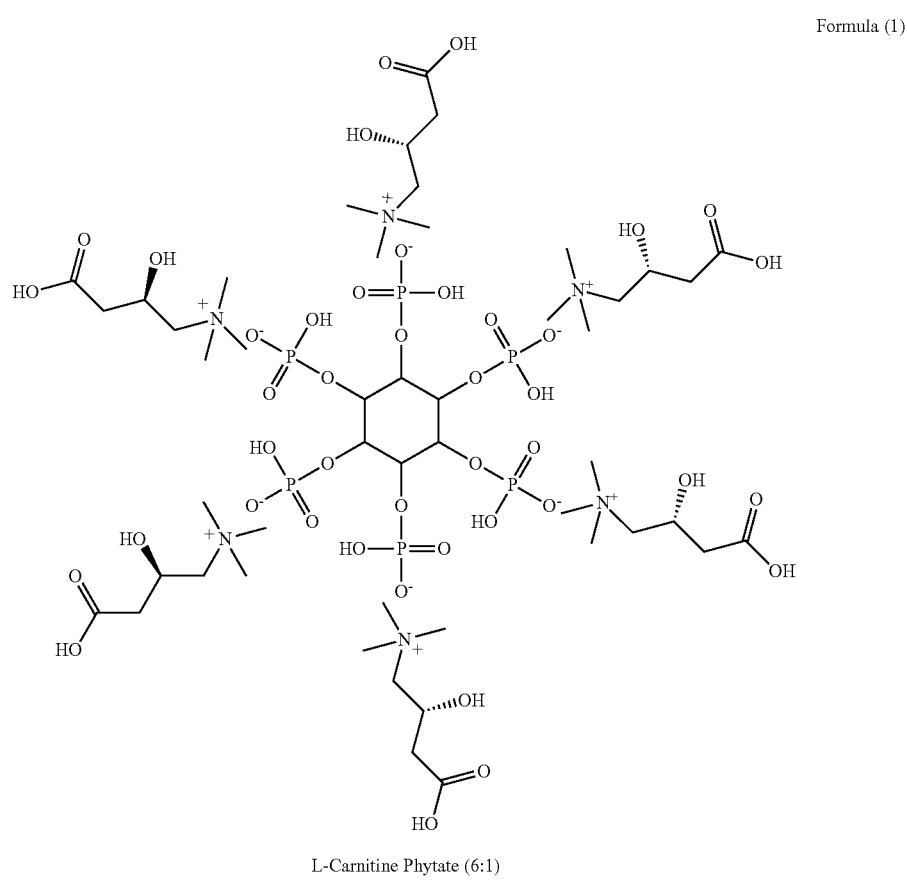
Formula (1)
L-Carnitine Phytate (6:1)

3.2. According to one embodiment, acetyl L-carnitine phytate (in a 6:1 mole ratio) ($C_{60}H_{120}N_6O_{48}P_6$, molecular weight 1879.44) is a six-directional dendrimer as shown by Formula (2):
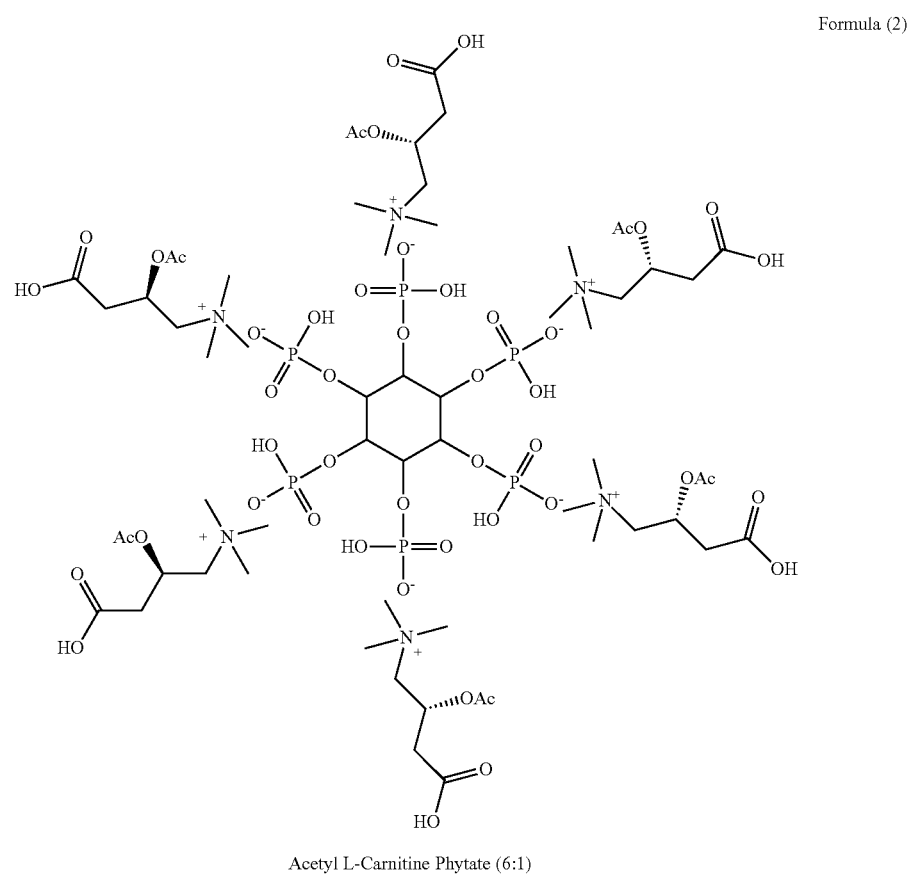
Acetyl L-Carnitine Phytate (6:1)
Formula (2)

3.3. According to one embodiment, propionyl L-carnitine phytate (in a 6:1 mole ratio) ($C_{66}H_{132}N_6O_{48}P_6$, molecular weight 1963.61) is a six-directional dendrimer as shown by Formula (3):
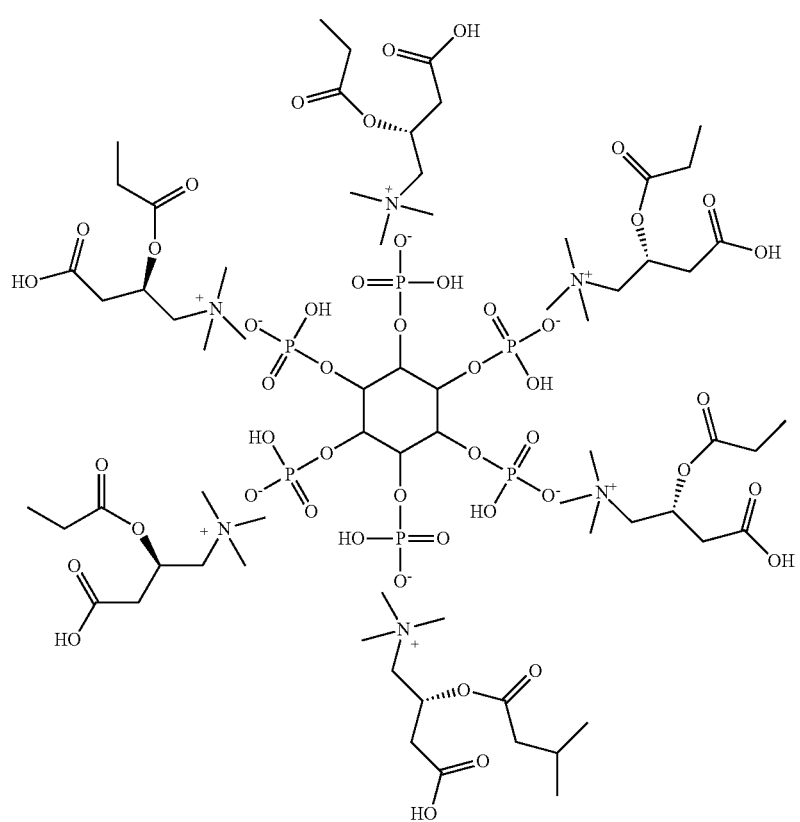
Formula (3)
Propionyl L-Carnitine Phytate (6:1)

3.4. According to one embodiment, butyryl L-carnitine phytate (in a 6:1 mole ratio) ($C_{72}H_{144}N_6O_{48}P_6$, molecular weight 2046.76) is a six-directional dendrimer as shown by Formula (4):
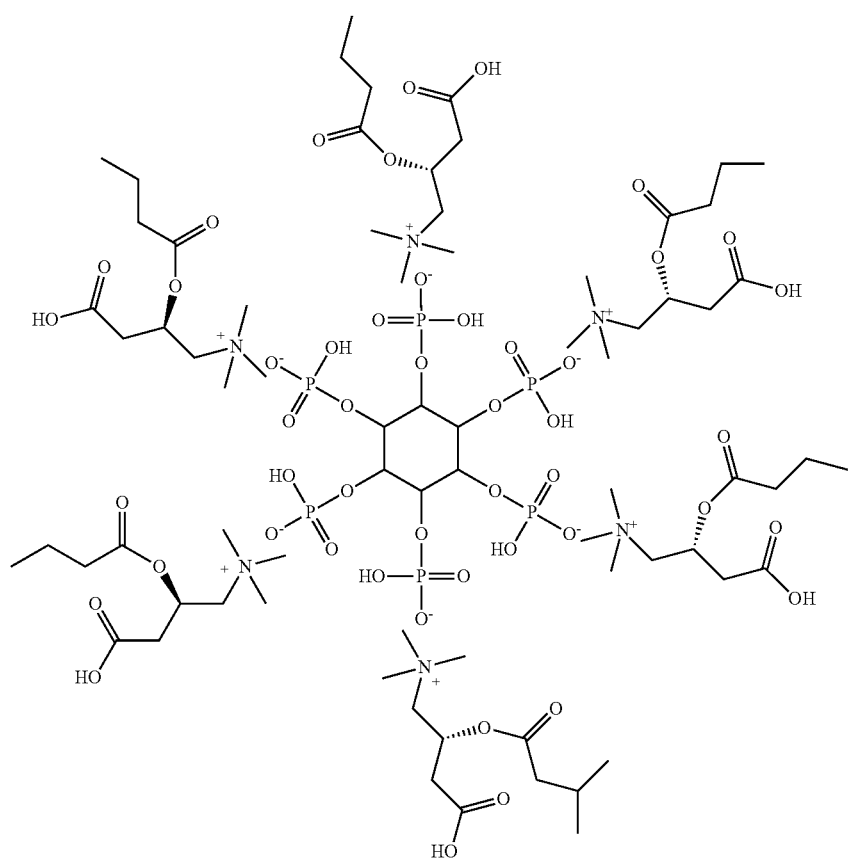
Butyryl L-Carnitine Phytate (6:1)

3.5. According to one embodiment, isobutyryl L-carnitine phytate (in a 6:1 mole ratio) ($C_{72}H_{144}N_6O_{48}P_6$, molecular weight 2046.76) is a six-directional dendrimer as shown by Formula (5):
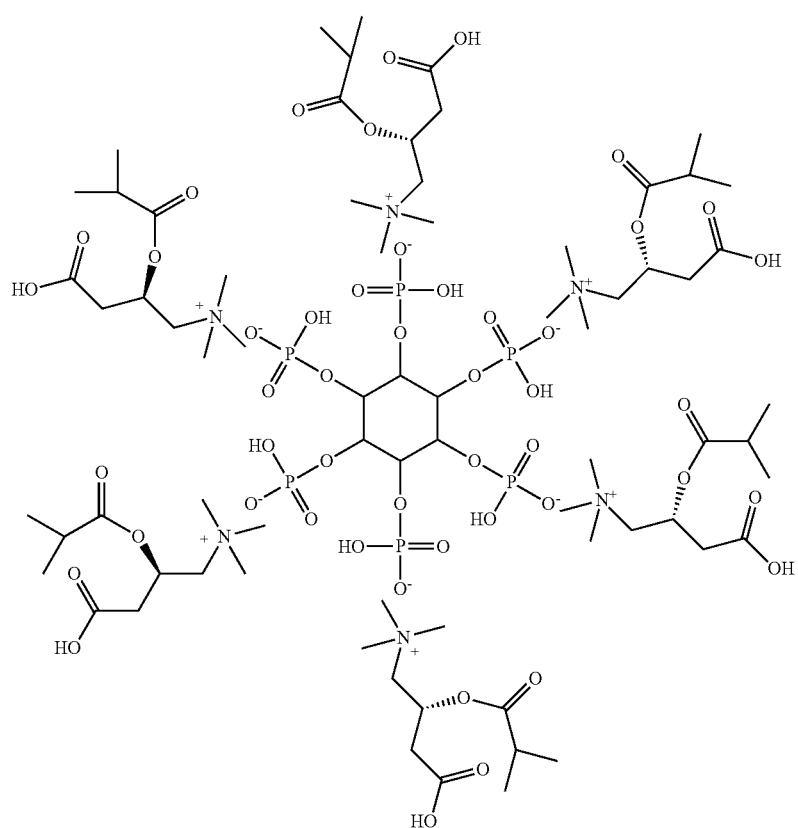
Isobutyryl L-Carnitine Phytate (6:1)
Formula (5)

3.6. According to one embodiment, valeryl L-carnitine phytate (in a 6:1 mole ratio) ($C_{78}H_{156}N_6O_{48}P_6$, molecular weight 2129.76) is a six-directional dendrimer as shown by Formula (6):
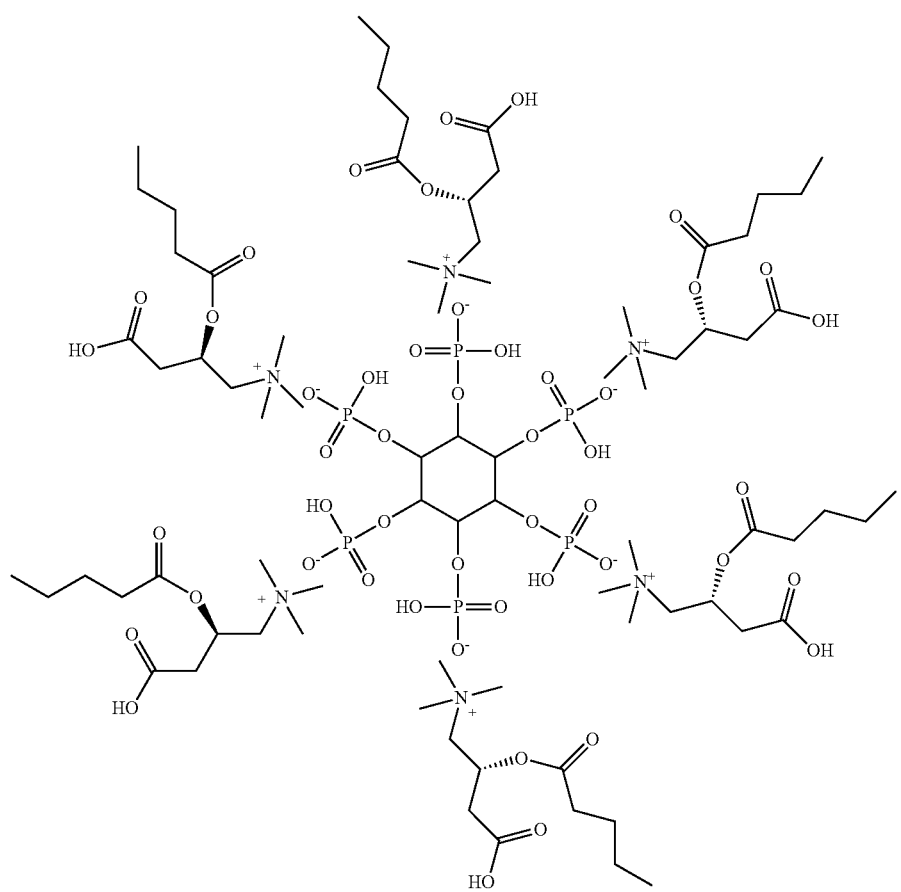
Formula (6)
Valeryl L-Carnitine Phytate (6:1)

3.7. According to one embodiment, isovaleryl L-carnitine phytate (in a 6:1 mole ratio) ($C_{78}H_{156}N_6O_{48}P_6$, molecular weight 2129.76) is a six-directional dendrimer as shown by Formula (7):

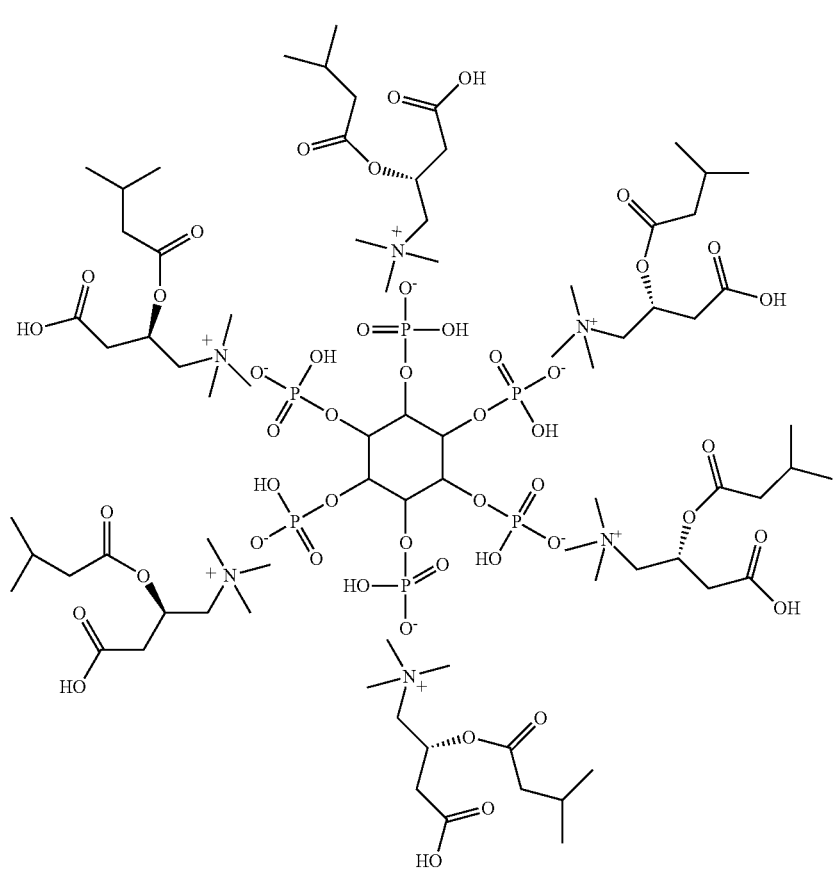

Isovaleryl L-Carnitine Phytate (6:1)

Formula (7)

4. Both cation moiety (i.e., L-carnitine or alkanoyl L-carnitines) and anion moiety (i.e., phytate) have various biologically beneficial properties, some of which are similar or the same, such as the antioxidant property as well as cardiovascular and immune system benefits. These biologically beneficial properties can reasonably be expected to be due to the synergistic efficacy of their salt form complex.

5. Phytic acid is a liquid substance (syrup), strongly acidic and not convenient for storage, processing, and consuming. However, when it is composed with L-carnitine or its alkanoyl derivatives inner salt, the salt form phytates are weakly acidic, and according to one embodiment, L-carnitine phytate (in a 6:1 mole ratio) and lower alkanoyl L-carnitine phytate (in a 6:1 mole ration), such as acetyl L-carnitine phytate (in a 6:1 mole ratio) and propionyl L-carnitine phytate (in a 6:1 mole ratio), are solid, and, thus easy to handle and use.

6. L-carnitine and its alkanoyl derivative inner salts are strongly hygroscopic, but according to one embodiment, their phytates (in a 6:1 mole ratio) are less hygroscopic, which is acceptable for processing and storage.

7. L-carnitine and its alkanoyl derivative hydrochlorides have unpleasant and irritating hydrochloric smells, which according to one embodiment, their phytates (in a 6:1 mole ratio) do not have.

8. According to one embodiment, L-carnitine and alkanoyl L-carnitine phytates (in a 6:1 mole ratio) are stable and almost odorless, without the unpleasant fishy smell given off by the inner salts (which is the emission of traces of amine that is usually generated by the decomposition of inner salts).

9. According to one embodiment, both L-carnitine or its alkanoyl derivatives and phytic acid as well as their salt form complexes are non-toxic and safe to consume.

Preparation of L-Carnitine and Alkanoyl L-Carnitine Phytates

According to one embodiment, L-carnitine phytates are produced by a reaction between an L-carnitine inner salt, or an alkanoyl L-carnitine inner salt, and phytic acid as shown by reaction Scheme (I):

Scheme (I)

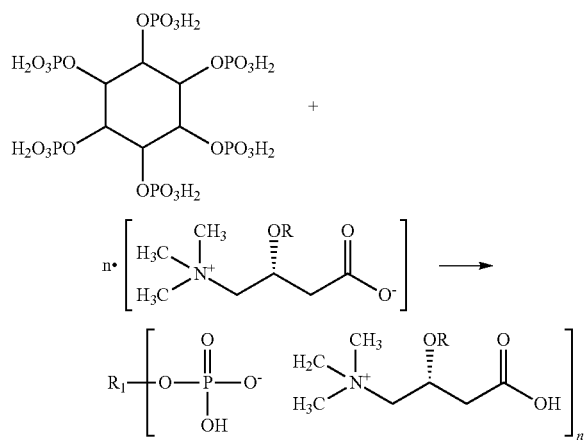

wherein n=1-6; $R_1$ is the phytate anion; and R is hydrogen, or a straight or branched-chain alkanoyl group having 2-12 carbon atoms. According to one embodiment, the alkanoyl group is a lower alkanoyl group having 2-5 carbon atoms. According to one embodiment, the alkanoyl group is selected from acetyl, propionyl, butyryl, isobutyryl, valeryl and isovaleryl groups.

According to one embodiment, L-carnitine or alkanoyl L-carnitine inner salt is added to an aqueous solution of phytic acid while stirring. According to one embodiment, the mole ratio between the combined L-carnitine or alkanoyl L-carnitine inner salt and phytic acid may range from a 1:1 mole ratio to a 6:1 mole ratio with the ratio depending on the desired purpose. According to one embodiment, after L-carnitine or alkanoyl L-carnitine inner salt is added to an aqueous solution of phytic acid and stirred about 15 minutes a clear solution is obtained. According to one embodiment, after L-carnitine or alkanoyl L-carnitine inner salt is added to an aqueous solution of phytic acid and stirred about 15 minutes a clear solution is obtained which is further stirred for another 20 minutes at the same conditions and then was dried in a vacuum to obtain the resulting product.

According to one embodiment, L-carnitine or alkanoyl L-carnitine phytate (in a 6:1 mole ratio) is prepared as shown by reaction Scheme (II):

Scheme (II)

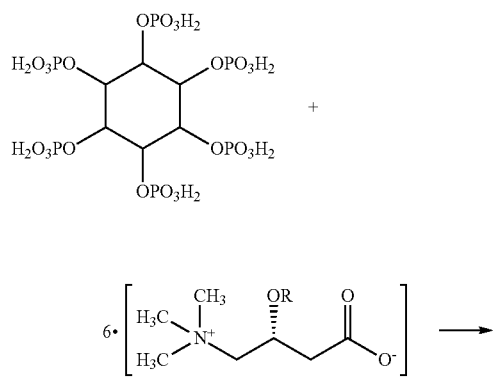

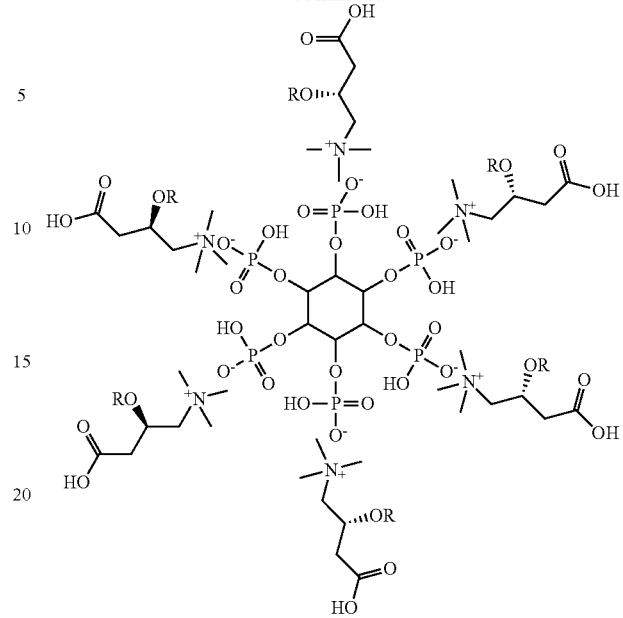

wherein R represents either a hydrogen or an alkanoyl group (either a straight or branched-chain alkanoyl group) having 2-12 carbon atoms. According to one embodiment, the alkanoyl group is a lower alkanoyl group having 2-5 carbon atoms. According to one embodiment, the alkanoyl group is selected from acetyl, propionyl, butyryl, isobutyryl, valeryl and isovaleryl groups.

According to one embodiment, a 6 times mole ratio of L-carnitine or alkanoyl L-carnitine inner salt is added to a 1 time mole ratio of 50% aqueous solution of phytic acid (having a pH value lower than 1) and stirred at 10-50 degrees Celsius. According to one embodiment, a 6 times mole ratio of L-carnitine or alkanoyl L-carnitine inner salt is added to a 1 time mole ratio of 50% aqueous solution of phytic acid (having a pH value lower than 1) and stirred at 10-50 degrees Celsius for about 15 minutes until a clear solution (having a pH value of 3-4) is obtained. According to one embodiment, the clear solution (having a pH value of 3-4) is stirred for an additional 20 minutes and then concentrated under a vacuum at 40-70 degrees Celsius. According to one embodiment, the residue is repeatedly taken up with anhydrous ethanol. According to one embodiment, the final residue is dried in a vacuum oven at 40-70 degrees Celsius to obtain the resultant product.

According to one embodiment, L-carnitine and alkanoyl L-carnitine phytate can be used for pharmaceutical, nutriceutical, and cosmetic purposes, including but not limited to antioxidants, improvement for immunity, anticancer, a treatment and/or cure of disease (for example, for cardiovascular disease, strokes, Alzheimer's disease, Down's syndrome, and various neuropathies), boosting brain functions, improving learning and memory capacities (including age associated memory impairment), an anti-aging supplement; athletic performance, weight loss, and an animal feed additive.

Since phytic acid (IP6) is a 6-phosphate form of inositol, it has been found to be absorbed almost instantly, transported intracellularly and dephosphorylated into lower inositol phosphates, which play important roles in signal transduction, so it is reasonable to conclude that inositol monophosphate (IP1), inositol diphosphate (IP2), inositol triphosphate (IP3), inositol tetraphosphate (IP4), and inositol pentaphosphate (IP5), all can be used as acids to react with inner salts of L-carnitine and alkanoyl L-carnitine to form the anion moiety of the salts. Accordingly, L-carnitine and alkanoyl L-carnitine inositol monphosphates, L-carnitine and alkanoyl L-carnitine inositol diphosphates, L-carnitine and alkanoyl L-carnitine inositol triphosphates, L-carnitine and alkanoyl L-carnitine inositol tetraphosphates, L-carnitine and alkanoyl L-carnitine inositol pentaphosphates are within the scope of certain particular embodiments of the present invention.

According to one embodiment, while the mole ratio between L-carnitine (or alkanoyl L-carnitine) and phytic acid is selected from within a range of a mole ratio of 1:1 to 6:1, for L-carnitine phytate salt and alkanoyl L-carnitine phytate salt, since there are 12 dissociation sites in one phytic acid molecule, a mole ratio larger than 6:1 (for example, 7:1 to 12:1) is also included in the scope of an embodiment.

The invention is further explained by the following example embodiments, which are provided for illustrative purpose only and are not to be construed as limiting the scope of the invention.

EXAMPLE EMBODIMENTS

Example Embodiment 1

Preparation of L-Carnitine Phytate (in a Mole Ratio of 1:1-6:1)

L-Carnitine Phytate (in a mole ratio of 1:1-6:1) is represented by Formula (8):

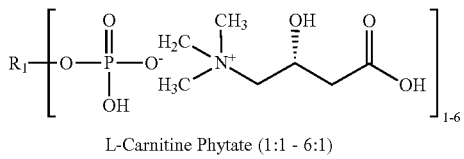

L-Carnitine Phytate (1:1 - 6:1)

Formula (8)

wherein $R_1$ represents the phytate anion.

According to one embodiment, 32.2 grams (0.2 mole) of L-carnitine inner salt ($C_7H_{15}NO_3$, molecular weight 161.20) are added to a 50% aqueous solution (pH value <1) of 66.0 gram (0.1 mole) phytic acid and stirred at room temperature resulting in an exothermic reaction. According to one embodiment, 32.2 grams (0.2 mole) of L-carnitine inner salt ($C_7H_{15}NO_3$, molecular weight 161.20) are added to a 50% aqueous solution (pH value <1) of 66.0 gram (0.1 mole) phytic acid and after stirred at room temperature for about 15 minutes creates a solution. According to one embodiment, the solution (having a pH value <1) was further stirred 20 minutes. According to one embodiment, the solution is concentrated on an evaporator under a vacuum at 50° C. According to one embodiment, the residue is repeatedly (3 times) taken up using anhydrous ethanol under a vacuum to dry the solution as much as possible. According to one embodiment, the residue is further dried in a vacuum oven at 50° C. to obtain 106.1 grams of residue from the mixture of L-carnitine phytate (1:1-6:1) and phytic acid, which appears clear, thick and sticky.

Example Embodiment 2

Preparation of L-Carnitine Phytate(in a 6:1 Mole Ratio)

L-Carnitine Phytate (in a 6:1 mole ratio) ($C_{48}H_{108}N_6O_{42}P_6$, molecular weight 1627.24) is represented by the formula shown by Formula (I).

According to one embodiment, 96.7 grams (0.6 mole) of L-carnitine inner salt ($C_7H_{15}NO_3$, molecular weight 161.20) was added to a 50% aqueous solution (having a pH value <1) of 66.0 grams (0.1 mole) phytic acid and stirred at room temperature resulting in an exothermic reaction. According to one embodiment, 96.7 grams (0.6 mole) of L-carnitine inner salt ($C_7H_{15}NO_3$, molecular weight 161.20) was added to a 50% aqueous solution (having a pH value <1) of 66.0 grams (0.1 mole) phytic acid and was stirred at room temperature for about 15 minutes to create a solution. According to one embodiment, the solution (having a pH value of about 4) was further stirred 20 minutes. According to one embodiment, the solution was concentrated on an evaporator under a vacuum at 50° C. According to one embodiment, the residue was repeatedly (3 times) taken up using anhydrous ethanol under a vacuum to dry the solution as much as possible. According to one embodiment, the residue is further dried in a vacuum oven at 50° C. to obtain 166.2 grams of white solid powder with an almost quantitative yield (i.e., the white solid powder contains 2% $H_2O$). According to one embodiment, this white solid powder has a melting point of 121-125 degrees Celsius (dec.), is odorless (i.e., it does not have the unpleasant fishy smell of L-carnitine inner salt that is usually generated by the decomposition of L-carnitine inner salt to emit amine), and has a pH value of 4 (c=1% $H_2O$), $^1HNMR$ ($D_2O$ ppm) δ=4.89, 4.46, and 4.24 (6H, m, CH—O—P), 4.64 (6H, m, CH—OH), 3.45 (12H, m, $CH_2N$), 3.20 (54H, s, $NCH_3$), 2.59 (12H, m, $CH_2COOH$).

Example Embodiment 3

Preparation of Acetyl L-Carnitine Phytate(in a 6:1 Mole Ratio)

Acetyl L-Carnitine Phytate (in a 6:1 mole ratio) ($C_{60}H_{120}N_6O_{48}P_6$, molecular weight 1879.44) is represented by Formula (2).

According to one embodiment, 122.09 grams (0.6 mole) of acetyl L-carnitine inner salt ($C_9H_{17}NO_4$, molecular weight 203.24) was added to a 50% aqueous solution (having a pH value <1) of 66.0 grams (0.1 mole) phytic acid and stirred at room temperature resulting in an exothermic reaction. According to one embodiment, 122.09 grams (0.6 mole) of acetyl L-carnitine inner salt ($C_9H_{17}NO_4$, molecular weight 203.24) was added to a 50% aqueous solution (having a pH value <1) of 66.0 grams (0.1 mole) phytic acid and was stirred at room temperature for about 15 minutes to create a solution. According to one embodiment, the solution (having a pH value of about 4) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 192.7 grams of white solid powder with an almost quantitative yield (i.e., the white solid powder contains 2% $H_2O$). According to one embodiment, this white solid powder has a melting point of 101-105 degrees Celsius (dec.), is odorless (i.e., it does not have the unpleasant hydrochloric smell of acetyl L-carnitine hydrochloride that is a commonly used salt form of acetyl L-carnitine), has a pH value of 4 (c=1% $H_2O$), $^1HNMR$ ($D_2O$ ppm) ε=5.59 (6H, m, CH—OAc), 4.88, 4.45, and 4.22 (6H, m, CH—O—P), 3.22 (12H, m, $CH_2N$), 3.16 (54H, s, $NCH_3$), 2.96 (12H, m, $CH_2COOH$), 2.11 (18H, s, $CH_3CO$).

Example Embodiment 4

Preparation of Propionyl L-Carnitine Phytate(in a 6:1 Mole Ratio)

Propinoyl L-Carnitine Phytate (in a 6:1 mole ratio) ($C_{66}H_{132}N_6O_{48}P_6$, molecular weight 1963.61) is represented by Formula (3).

According to one embodiment, 130.4 grams (0.6 mole) of propinoyl L-carnitine inner salt ($C_{10}H_{19}NO_4$, molecular weight 217.26) was added to a 50% aqueous solution (having a pH value <1) of 66.0 grams (0.1 mole) phytic acid and stirred at room temperature resulting in an exothermic reaction. According to one embodiment, 130.4 grams (0.6 mole) of propinoyl L-carnitine inner salt ($C_{10}H_{19}NO_4$, molecular weight 217.26) was added to a 50% aqueous solution (having a pH value <1) of 66.0 grams (0.1 mole) phytic acid and was stirred at room temperature for about 15 minutes to create a solution. According to one embodiment, the solution (having a pH value of about 3.5) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 201.3 grams of white solid powder with an almost quantitative yield (i.e., the white solid powder contains 2% $H_2O$). According to one embodiment, this white solid powder has a melting point of 85-90 degrees Celsius (dec.), is odorless (i.e., it does not have the unpleasant hydrochloric smell of propionyl L-carnitine hydrochloride that is a commonly used salt form of propionyl L-carnitine), and has a pH value of 4 (c=1% $H_2O$), $^1$HNMR ($D_2O$ ppm) δ=5.60 (6H, m, CH—O-Propionyl), 4.88, 4.46, and 4.22 (6H, m, CH—O—P), 3.22 (12H, m, $CH_2N$), 3.16 (54H, s, $NCH_3$), 2.96 (12H, m, $CH_2COOH$), 2.41 (12H, q, $CH_3CH_2CO$), 1.07 (18H, t, $CH_3CH_2CO$).

Example Embodiment 5

Preparation of Butyryl L-Carnitine Phytate(in a 6:1 Mole Ratio)

Butyryl L-Carnitine Phytate (in a 6:1 mole ratio) ($C_{72}H_{144}N_6O_{48}P_6$, molecular weight 2046.76) is represented by Formula (4).

According to one embodiment, 138.8 grams (0.6 mole) of butyryl L-carnitine inner salt ($C_{11}H_{21}NO_4$, molecular weight 231.26) was added to a 50% aqueous solution (having a pH value <1) of 66.0 grams (0.1 mole) phytic acid and stirred at room temperature resulting in an exothermic reaction. According to one embodiment, 138.8 grams (0.6 mole) of butyryl L-carnitine inner salt ($C_{11}H_{21}NO_4$, molecular weight 231.26) was added to a 50% aqueous solution (having a pH value <1) of 66.0 grams (0.1 mole) phytic acid and was stirred at room temperature for about 15 minutes to create a solution. According to one embodiment, the solution (having a pH value of about 3.8) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 209.5 grams of transparent gel-like product with an almost quantitative yield (i.e., the transparent gel-like product contains 2.24% $H_2O$). According to one embodiment, this transparent gel-like product has a pH value of 4 (c=1% $H_2O$), $^1$HNMR ($D_2O$ ppm) δ=5.62 (6H, m, CH—O-Butyryl), 4.85, 4.43, and 4.21 (6H, m, CH—O—P), 3.21 (12H, m, $CH_2N$), 3.14 (54H, s, $NCH_3$), 2.98 (12H, m, $CH_2COOH$), 2.41 (12H, t, $CH_3CH_2CH_2CO$), 1.21 (12H, m, $CH_3CH_2CH_2CO$), 1.08 (18H, t, $CH_3CH_2CH_2CO$).

Example Embodiment 6

Preparation of Isobutyryl L-Carnitine Phytate(in a 6:1 Mole Ratio)

Isobutyryl L-Carnitine Phytate (in a 6:1 mole ratio) ($C_{72}H_{144}N_6O_{48}P_6$, molecular weight 2046.76) is represented by Formula (5).

According to one embodiment, 34.7 grams (0.15 mole) of isobutyryl L-carnitine inner salt ($C_{11}H_{21}NO_4$, molecular weight 231.26) was added to a 50% aqueous solution (having a pH value <1) of 16.5 grams (0.025 mole) phytic acid and stirred at room temperature resulting in an exothermic reaction. According to one embodiment, 34.7 grams (0.15 mole) of isobutyryl L-carnitine inner salt ($C_{11}H_{21}NO_4$, molecular weight 231.26) was added to a 50% aqueous solution (having a pH value <1) of 16.5 grams (0.025 mole) phytic acid and was stirred at room temperature for about 15 minutes to create a solution. According to one embodiment, the solution (having a pH value of about 3.7) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 52.8 grams of transparent gel-like product with an almost quantitative yield (i.e., the transparent gel-like product contains 3% H2O). According to one embodiment, this transparent gel-like product has a pH of 4 (c=1% $H_2O$), $^1$HNMR ($D_2O$ ppm) δ=5.68 (6H, m, CH—O-isoButyryl), 4.88, 4.40, and 4.11 (6H, m, CH—O—P), 3.21 (12H, m, $CH_2N$), 3.14 (54H, s, $NCH_3$), 2.98 (12H, m, $CH_2COOH$), 2.31 (6H, m, $(CH_3)_2$CHCO), 1.06 (36H, d, $(CH_3)_2$CHCO).

Example Embodiment 7

Preparation of Valeryl L-Carnitine Phytate(in a 6:1 Mole Ratio)

Valeryl L-Carnitine Phytate (in a 6:1 mole ratio) ($C_{78}H_{156}N_6O_{48}P_6$, molecular weight 2129.76) is represented by Formula (6).

According to one embodiment, 24.5 grams (0.1 mole) of valeryl L-carnitine inner salt ($C_{12}H_{23}NO_4$, molecular weight 245.32) was added to a 50% aqueous solution (having a pH value <1) of 11.0 grams (0.0166 mole) phytic acid and stirred at room temperature resulting in an exothermic reaction. According to one embodiment, 24.5 grams (0.1 mole) of valeryl L-carnitine inner salt ($C_{12}H_{23}NO_4$, molecular weight 245.32) was added to a 50% aqueous solution (having a pH value <1) of 11.0 grams (0.0166 mole) phytic acid and was stirred at room temperature for about 15 minutes to create a solution. According to one embodiment, the solution (having a pH value of about 3.5) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 36.56 grams of transparent gel-like product with an almost quantitative yield (i.e., the transparent gel-like product contains 2.9% $H_2O$). According to one embodiment, this transparent gel-like product has a pH value of 4 (c=1% $H_2O$), $^1$HNMR ($D_2O$ ppm) ∈=5.59 (6H, m, CH—O-Valeryl), 4.85, 4.43, and 4.21 (6H, m, CH—O—P), 3.19 (12H, m, $CH_2N$), 3.13 (54H, s, $NCH_3$), 2.99 (12H, m, $CH_2COOH$), 2.44 (12H, t, $CH_3CH_2CH_2CH_2CO$), 1.21-1.29 (24H, m, $CH_3CH_2CH_2CH_2CO$), 1.08 (18H, t, $CH_3CH_2CH_2CO$).

Example Embodiment 8

Preparation of Isovaleryl L-Carnitine Phytate(in a 6:1 Mole Ratio)

Isovaleryl L-Carnitine Phytate (in a 6:1 mole ratio) ($C_{78}H_{156}N_6O_{48}P_6$, molecular weight 2129.76) is represented by Formula (7).

According to one embodiment, 12.25 grams (0.05 mole) of isovaleryl L-carnitine inner salt ($C_{12}H_{23}NO_4$, molecular weight 245.32) was added to a 50% aqueous solution (having a pH value <1) of 5.5 grams (0.0083 mole) phytic acid and stirred at room temperature resulting in an exothermic reaction. According to one embodiment, 12.25 grams (0.05 mole) of isovaleryl L-carnitine inner salt ($C_{12}H_{23}NO_4$, molecular weight 245.32) was added to a 50% aqueous solution (having a pH value <1) of 5.5 grams (0.0083 mole) phytic acid and was stirred at room temperature for about 15 minutes to create a solution. According to one embodiment, the solution (having a pH value of about 3.5) was further stirred 20 minutes. According to one embodiment, the solution is concentrated on an evaporator under a vacuum at 50° C. According to one embodiment, the residue was repeatedly (3 times) taken up with anhydrous ethanol in a vacuum to dry the residue as much as possible. According to one embodiment, the residue is further dried in a vacuum oven at 50° C. to obtain 18.3 grams of transparent gel-like product with an almost quantitative yield (i.e., the transparent gel-like product contains 3.0% $H_2O$). According to one embodiment, this transparent gel-like product has a pH value of 4 (c=1% $H_2O$), $^1$HNMR ($D_2O$ ppm) δ=5.56 (6H, m, CH—O-isovaleryl), 4.86, 4.43, and 4.21 (6H, m, CH—O—P), 3.18 (12H, m, $CH_2N$), 3.11 (54H, s, $NCH_3$), 2.98 (12H, m, $CH_2COOH$), 2.43 (12H, d, $(CH_3)_2CH_1CH_2CO$), 1.20-1.26 (6H, m, $(CH_3)_2CH_1CH_2CO$), 1.05 (36H, d, $(CH_3)_2CH_1CH_2CO$).

Example Embodiment 9

Acute Toxicity Study ($LD_{50}$) of L-Carnitine Phytate(in a 6:1 Mole Ratio)

The single dose oral acute toxicity of L-carnitine phytate (in a 6:1 mole ratio) was evaluated in mice. Five dosages (25, 20, 15, 10, and 5 g/Kg) were orally administrated to five groups of mice in which each group had five male and five female mice. After dosing, the five groups of mice were observed and daily records (for 14 days) were made of their general conditions, toxic response, and deaths. All of the dead mice were necropsied, in which each of the body's thorace and abdomen were opened, and each heart, liver, spleen, lung, kidney, and intestine were examined and recorded. Under the conditions of this test, the acute oral LD50 of L-carnitine phytate (6:1) was determined to be 14.86 g/Kg in the mice. Moreover, there were not any obvious abnormalities observed in the hearts, livers, spleens, lungs, kidneys, and intestines studied.

While the above detailed description and example embodiments have shown, described and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description and example embodiments. All changes which come within the meaning and range of equivalency of the claims are to be embraced within their scope.

I claim:

1. A salt comprising at least one of L-carnitine or alkanoyl L-carnitine, and phytic acid, having general formula (I):

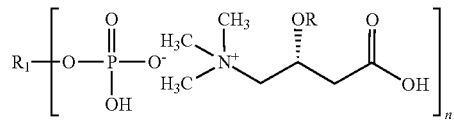

wherein:

n=1-6;

$R_1$ is a phytate anion; and

R comprises at least one of a hydrogen atom, a straight alkanoyl group having 2-12 carbon atoms, and a branched-chain alkanoyl group having 2-12 carbon atoms.

2. The salt of claim 1, wherein R comprises either a straight alkanoyl group having 2-5 carbon atoms, or a branched-chain alkanoyl group having 2-5 carbon atoms.

3. The salt of claim 1, wherein R comprises either a straight alkanoyl group, or a branched-chain alkanoyl group in which the alkanoyl group is selected from the group consisting of acetyl, propionyl, butyryl, isobutyryl, valeryl and isovaleryl.

4. The salt of claim 1, wherein n is 6, having general formula (II):

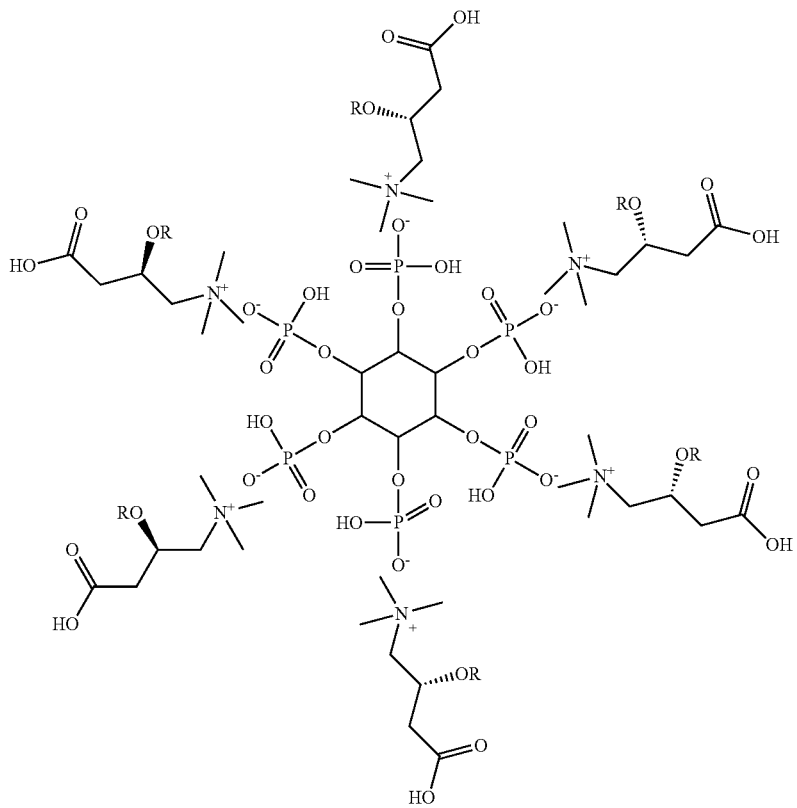

wherein:
R comprises at least one of hydrogen, a straight alkanoyl group having 2-12 carbon atoms, and a branched-chain alkanoyl group having 2-12 carbon atoms.

5. The salt of claim 4, wherein R comprises either a straight alkanoyl group having 2-5 carbon atoms, or a branched-chain alkanoyl group having 2-5 carbon atoms.

6. The salt of claim 5, wherein R is selected from the group consisting of hydrogen, acetyl, propionyl, butyryl, isobutyryl, valeryl and isovaleryl.

7. The salt of claim 4, wherein R is selected from the group consisting of hydrogen, acetyl, propionyl, butyryl, isobutyryl, valeryl and isovaleryl.

8. The salt of claim 7, wherein the salt is selected from the group consisting of L-carnitine phytate (in a 6:1 mole ratio), Acetyl L-carnitine phytate (in a 6:1 mole ratio), Propionyl L-carnitine phytate (in a 6:1 mole ratio), Butyryl L-carnitine phytate (in a 6:1 mole ratio), Isobutyryl L-carnitine phytate (in a 6:1 mole ratio), Valeryl L-carnitine phytate (in a 6:1 mole ratio) and Isovaleryl L-carnitine phytate (in a 6:1 mole ratio).

9. A process for preparing the salt of claim 1 comprising: combining at least one of L-carnitine inner salt and alkanoyl L-carnitine inner salt, and phytic acid, wherein the mole ratio of inner salt to phytic acid is within the range of 1:1 to 6:1.

10. A process for preparing the salt of claim 4 comprising: combining at least one of L-carnitine inner salt and alkanoyl L-carnitine inner salt, and phytic acid, wherein the mole ratio of inner salt to phytic acid is 6:1.

11. A process for preparing L-carnitine phytate (in a 6:1 mole ratio) of claim 8, comprising combining L-carnitine inner salt and phytic acid, wherein the mole ratio of inner salt to phytic acid is 6:1.

12. A process for preparing Acetyl L-carnitine phytate (in a 6:1 mole ratio) of claim 8, comprising combining acetyl L-carnitine inner salt and phytic acid, wherein the mole ratio of inner salt to phytic acid is 6:1.

13. A process for preparing Propionyl L-carnitine phytate (in a 6:1 mole ratio) of claim 8, comprising combining propionyl L-carnitine inner salt and phytic acid, wherein the mole ratio of inner salt to phytic acid is 6:1.

14. A process for preparing Butyryl L-carnitine phytate (in a 6:1 mole ratio) of claim 8, comprising combining butyryl L-carnitine inner salt and phytic acid, wherein the mole ratio of inner salt to phytic acid is 6:1.

15. A process for preparing Isobutyryl L-carnitine phytate (in a 6:1 mole ratio) of claim 8, comprising combining isobutyryl L-carnitine inner salt and phytic acid, wherein the mole ratio of inner salt to phytic acid is 6:1.

16. A process for preparing Valeryl L-carnitine phytate (in a 6:1 mole ratio) of claim 8, comprising combining valeryl L-carnitine inner salt and phytic acid, wherein the mole ratio of inner salt to phytic acid is 6:1.

17. A process for preparing Isovaleryl L-carnitine phytate (in a 6:1 mole ratio) of claim 8, comprising combining isovaleryl L-carnitine inner salt and phytic acid, wherein the mole ratio of inner salt to phytic acid is 6:1.

* * * * *